United States Patent [19]

Hodges et al.

[11] Patent Number: 5,942,102
[45] Date of Patent: Aug. 24, 1999

[54] ELECTROCHEMICAL METHOD

[75] Inventors: Alastair McIndoe Hodges, Blackburn South Victoria; Thomas William Beck, South Windsor; Oddvar Johansen, Mulgrave; Ian Andrew Maxwell, Leichhardt, all of Australia

[73] Assignee: USF Filtration and Separations Group Inc., Timonium, Md.

[21] Appl. No.: 08/852,804

[22] Filed: May 7, 1997

[30] Foreign Application Priority Data

Nov. 15, 1996 [WO] WIPO ............... PCT/AU96/00723

[51] Int. Cl.⁶ .................................................. G01N 27/26
[52] U.S. Cl. .................. 205/775; 205/777.5; 205/778; 205/780.5; 205/782.5; 205/792
[58] Field of Search ............................ 205/775, 777.5, 205/778, 780.5, 782, 782.5, 792

[56] References Cited

U.S. PATENT DOCUMENTS

| | | | |
|---|---|---|---|
| 4,224,125 | 9/1980 | Nakamura et al. | 204/195 B |
| 4,233,029 | 11/1980 | Columbus | 23/230 R |
| 4,254,083 | 3/1981 | Columbus | 422/55 |
| 4,259,165 | 3/1981 | Miyake | 204/415 |
| 4,301,412 | 11/1981 | Hill et al. | 324/442 |
| 4,301,414 | 11/1981 | Hill et al. | 324/446 |
| 4,303,887 | 12/1981 | Hill et al. | 324/441 |
| 4,307,188 | 12/1981 | White | 435/4 |
| 4,374,013 | 2/1983 | Enfors | 204/195 |
| 4,404,066 | 9/1983 | Johnson | 205/778 |
| 4,431,004 | 2/1984 | Bessman et al. | 128/635 |
| 4,517,287 | 5/1985 | Scheibe et al. | 435/4 |
| 4,517,291 | 5/1985 | Seago | 435/14 |
| 4,533,440 | 8/1985 | Kim | 204/1 |
| 4,545,382 | 10/1985 | Higgins et al. | 128/635 |
| 4,552,840 | 11/1985 | Riffer | 205/778 |
| 4,629,563 | 12/1986 | Wrasidlo | 210/500.34 |
| 4,654,197 | 3/1987 | Lilja et al. | 422/56 |
| 4,664,119 | 5/1987 | Bessman et al. | 204/415 |
| 4,711,245 | 12/1987 | Higgins et al. | 128/635 |
| 4,774,039 | 9/1988 | Wrasidlo | 264/41 |
| 4,790,925 | 12/1988 | Miller et al. | 204/415 |
| 4,900,424 | 2/1990 | Birth et al. | 204/409 |
| 4,919,770 | 4/1990 | Preidel et al. | 204/153.1 |
| 4,963,815 | 10/1990 | Hafeman | 205/777.5 |
| 5,059,908 | 10/1991 | Mina | 324/444 |
| 5,064,516 | 11/1991 | Rupich | 204/415 |
| 5,120,420 | 6/1992 | Nankai et al. | 204/403 |
| 5,122,244 | 6/1992 | Hoenes et al. | 204/153.1 |
| 5,126,034 | 6/1992 | Carter et al. | 204/403 |
| 5,128,015 | 7/1992 | Szuminsky et al. | 205/782.5 |
| 5,141,868 | 8/1992 | Shanks et al. | 435/288 |
| 5,151,166 | 9/1992 | Harral et al. | 204/425 |
| 5,192,415 | 3/1993 | Yoshioka et al. | 204/403 |
| 5,229,282 | 7/1993 | Yoshioka et al. | 435/177 |
| 5,272,087 | 12/1993 | El Murr et al. | 435/291 |
| 5,320,732 | 6/1994 | Nankai et al. | 204/403 |
| 5,382,346 | 1/1995 | Uenoyama et al. | 204/403 |
| 5,384,028 | 1/1995 | Ito | 204/403 |
| 5,385,846 | 1/1995 | Kuhn et al. | 436/70 |
| 5,393,399 | 2/1995 | Van Den Berg et al. | 204/412 |
| 5,413,690 | 5/1995 | Kost et al. | 204/403 |
| 5,437,999 | 8/1995 | Diebold et al. | 435/288 |
| 5,508,171 | 4/1996 | Walling et al. | 205/777.5 |
| 5,509,410 | 4/1996 | Hill et al. | 128/637 |
| 5,527,446 | 6/1996 | Kosek et al. | 204/415 |
| 5,567,302 | 10/1996 | Song et al. | 205/777.5 |
| 5,611,908 | 3/1997 | Matthiessen et al. | 205/775 |
| 5,620,579 | 4/1997 | Genshaw et al. | 205/775 |
| 5,628,890 | 5/1997 | Carter et al. | 204/403 |
| 5,645,709 | 7/1997 | Birch et al. | 205/775 |

FOREIGN PATENT DOCUMENTS

| | | |
|---|---|---|
| A 54873/94 | 2/1993 | Australia . |
| A 31042/93 | 7/1993 | Australia . |
| 0 251 915 A2 | 1/1988 | European Pat. Off. . |
| 0 255 291 A1 | 2/1988 | European Pat. Off. . |
| 0 266 204 A2 | 4/1988 | European Pat. Off. . |
| 0 278 647 A2 | 8/1988 | European Pat. Off. . |
| 0 299 779 A2 | 1/1989 | European Pat. Off. . |
| 0 351 516 A2 | 1/1990 | European Pat. Off. . |
| 0 351 892 A2 | 1/1990 | European Pat. Off. . |
| 0 171 375 A1 | 5/1990 | European Pat. Off. . |
| 0 400 918 A1 | 12/1990 | European Pat. Off. . |
| 0 418 404 A1 | 3/1991 | European Pat. Off. . |
| 0 451 981 A2 | 10/1991 | European Pat. Off. . |
| 0 560 336 A1 | 9/1993 | European Pat. Off. . |
| 3103 464 A1 | 8/1982 | Germany . |
| 3103-464 | 8/1982 | Germany . |
| 62-228274 | 10/1987 | Japan . |
| 3-167464 | 7/1991 | Japan . |
| 4-66112 | 3/1992 | Japan . |
| 1351-627 | 11/1987 | U.S.S.R. . |
| 2 020 424 | 11/1979 | United Kingdom . |
| 2 154 735 | 9/1985 | United Kingdom . |
| 2 201 248 | 8/1988 | United Kingdom . |
| 2 235 050 | 2/1991 | United Kingdom . |
| WO 89/08713 | 9/1989 | WIPO . |
| WO 92/15701 | 9/1992 | WIPO . |
| WO 94/02842 | 2/1994 | WIPO . |
| WO 95/16198 | 6/1995 | WIPO . |
| WO 97/00441 | 1/1997 | WIPO . |

OTHER PUBLICATIONS

Derwent Abstract Accession No. 92 119462/15, Class S03, JP, A, 04–62463 (Tokyo Yogyo K.K.) Feb. 27, 1992.

Patent Abstracts of Japan, P–269, p. 166, JP, A,59–3345 (Hitachi Seisakusho K.K.) Jan. 10, 1994.

*Primary Examiner*—Bruce F. Bell
*Attorney, Agent, or Firm*—Knobbe, Martens, Olson & Bear, LLP

[57] ABSTRACT

A method for determining the concentration of a reduced or oxidized form of a redox species in an electrochemical cell (FIG. 10) of the kind comprising a working electrode (2) and a counter electrode (16) spaced from the working electrode such that reaction products from the counter electrode arrive at the working electrode, the method comprising the steps (FIG. 5) of applying (21) an electric potential between the electrodes, such that the electro-oxidation of the redox species is diffusion controlled, determining the current as a function of time, estimating the magnitude of the steady state current (23), reversing the potential, again determining current as a function of time and estimating the reverse potential steady state (25).

14 Claims, 9 Drawing Sheets

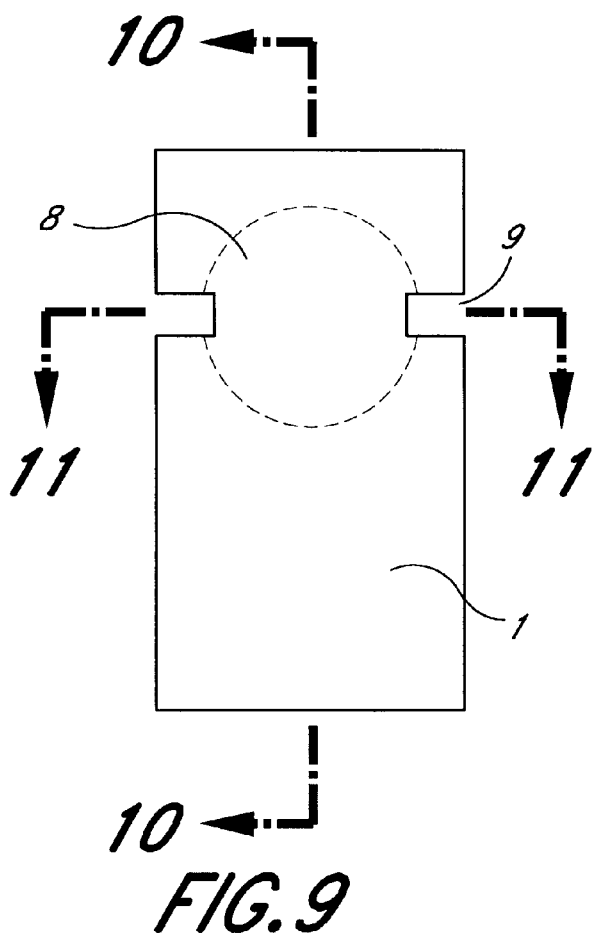
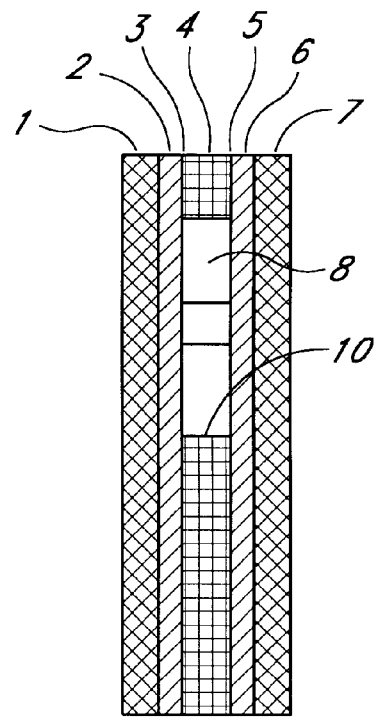
FIG. 9    FIG. 10
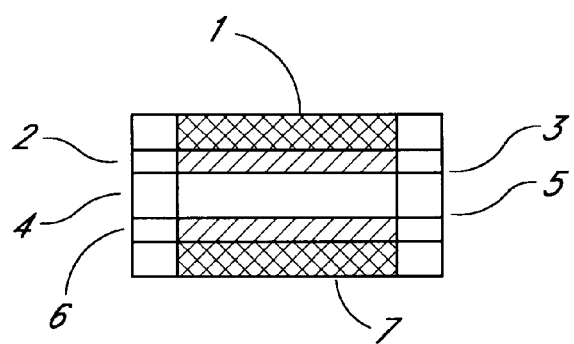
FIG. 11

ELECTROCHEMICAL METHOD

FIELD OF THE INVENTION

This invention relates to an electrochemical method for determining the concentration of an analyte in a carrier and to apparatus suitable for use in conducting the method.

BACKGROUND ART

The invention herein described is an improvement in or modification of the invention described in our co-pending application PCT/AU96/00365, the contents of which are incorporated herein by reference.

The invention will herein be described with particular reference to a biosensor adapted to measure the concentration of glucose in blood, but it will be understood not to be limited to that particular use and is applicable to other analytic determinations.

It is known to measure the concentration of a component to be analysed in an aqueous liquid sample by placing the sample into a reaction zone in an electrochemical cell comprising two electrodes having an impedance which renders them suitable for amperometric measurement. The component to be analysed is allowed to react directly with an electrode, or directly or indirectly with a redox reagent whereby to form an oxidisable (or reducible) substance in an amount corresponding to the concentration of the component to be analysed. The quantity of the oxidisable (or reducible) substance present is then estimated electrochemically. Generally this method requires sufficient separation of the electrodes so that electrolysis products at one electrode cannot reach the other electrode and interfere with the processes at the other electrode during the period of measurement.

In our co-pending application we described a novel method for determining the concentration of the reduced (or oxidised) form of a redox species in an electrochemical cell of the kind comprising a working electrode and a counter (or counter/reference) electrode spaced from the working electrode. The method involves applying an electrical potential difference between the electrodes, spacing the working electrode from the counter electrode so that reaction products from the counter electrode arrive at the working electrode and selecting the potential of the working electrode so that the rate of electro-oxidation of the reduced form of the species (or of electro-reduction of the oxidised form) is diffusion controlled. By determining the current as a function of time after application of the potential and prior to achievement of a steady state current and then estimating the magnitude of the steady state current, the method previously described allows the diffusion coefficient and/or the concentration of the reduced (or oxidised) form of the species to be estimated.

Our co-pending application exemplifies this method with reference to use of a "thin layer" cell employing a GOD/Ferrocyanide system. As herein used, the term "thin layer electrochemical cell" refers to a cell having closely spaced electrodes such that reaction products from the counter electrode arrive at the working electrode. In practice, the separation of electrodes in such a cell for measuring glucose in blood will be less than 500 microns, and preferably less than 200 microns.

The chemistry used in the exemplified electrochemical cell is as follows:

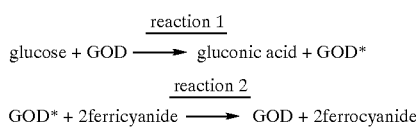

where GOD is the enzyme glucose oxidase, and GOD* is the 'activated' enzyme. Ferricyanide ($[Fe(CN)_6]^{3-}$) is the 'mediator' which returns the GOD* to its catalytic state. GOD, an enzyme catalyst, is not consumed during the reaction so long as excess mediator is present. Ferrocyanide ($[Fe(CN)_6]^{4-}$) is the product of the total reaction. Ideally there is initially no ferrocyanide, although in practice there is often a small quantity. After reaction is complete the concentration of ferrocyanide (measured electrochemically) indicates the initial concentration of glucose. The total reaction is the sum of reactions 1 and 2:

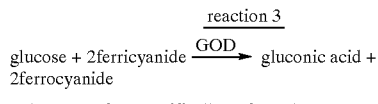

"Glucose" refers specifically to β-D-glucose.

The prior art suffers from a number of disadvantages. Firstly, sample size required is greater than desirable. It would be generally preferable to be able to make measurements on samples of reduced volume since this in turn enables use of less invasive methods to obtain samples.

Secondly, it would be generally desirable to improve the accuracy of measurement and to eliminate or reduce variations due, for example, to cell asymmetry or other factors introduced during mass production of microcells.

Thirdly, it would be generally desirable to reduce the time that is required in which to obtain a measurement. The test protocols used in current commercially available electrochemical glucose sensors involve a predetermined wait period at the beginning of the test during which the enzyme reacts with the glucose to produce the specie that is sensed electrochemically. This initial period is fixed at the maximum necessary to achieve the desired reaction under all conditions of use.

Fourthly, it would be desirable to eliminate variations due to oxygen. Oxygen can be plentiful in blood, either dissolved in the plasma, or bound in hemoglobin. It can also be introduced during "finger sticking", where a blood drop of small volume and high surface area is exposed to the atmosphere prior to introduction to a cell. Oxygen can interfere since oxygen is a mediator for GOD. The reaction is as follows:

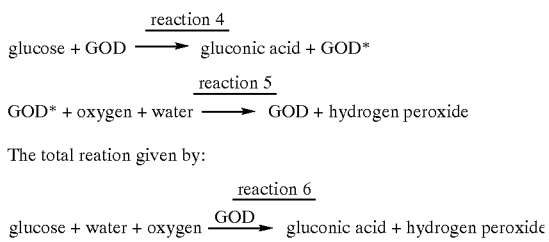

In most situations the complication of oxygen also acting as a mediator is unwanted, simply because the concentration of final ferrocyanide no longer is directly proportional to the concentration of initial glucose. Instead, the initial glucose concentration is then related to both the final concentration of ferrocyanide and of hydrogen peroxide.

OBJECT OF THE INVENTION

An object of the invention is to provide an improved method for determination of the concentration of an analyte in a carrier which avoids or ameliorates the disadvantages of prior art. It is an object of preferred forms of the invention to provide a biosensor of improved accuracy, and/or reliability and/or speed.

DISCLOSURE OF THE INVENTION

According to one aspect the invention consists in a method for determining the concentration of a reduced (or oxidised) form of a redox species in an electrochemical cell of the kind comprising a working electrode and a counter electrode spaced from the working electrode by a predetermined distance, said method comprising the steps of:
(a) applying an electric potential between the electrodes, wherein the electrodes are spaced so that reaction products from the counter electrode arrive at the working electrode by diffusion and wherein the potential of the working electrode is such that the rate of the electro-oxidation of the reduced form (or oxidised form) of the redox species is diffusion controlled,
  (b) determining current as a function of time after application of the potential and prior to achievement of a steady state,
  (c) estimating the magnitude of the steady state current,
  (d) interrupting, or reversing the polarity, of the potential,
  (e) repeating step (b) and step (c).

The invention stems from the discovery that if the polarity is reversed (ie the anode becomes the cathode and vice versa) after the initial steady state current is achieved, then a second transient current can be observed and after a period of time a second steady state is achieved. This has proved useful for diagnosing, and for reducing the effects of, cell asymmetry and other factors which influence the transient current. It also permits greater reliability and/or accuracy of estimation by allowing measurements to be made repetitively using reverse polarities. Likewise if the potential is interrupted for a time sufficient for the concentration profile to relax to a random state and is then reapplied, steps (b) and (c) can be repeated.

According to a second aspect the invention consists in a method according to the first aspect for measuring the concentration of glucose in a sample by means of a cell having a working electrode, a counter electrode, an enzyme catalyst and a redox mediator, comprising the steps of operating the cell at a potential higher than that of the redox reaction so as to oxidise hydrogen peroxide at the anode and then conducting a method according to the first aspect.

By this means the interference of oxygen can be ameliorated as explained in more detail hereinafter.

According to a third aspect the invention consists in a method according to the first or second aspect wherein the sample is allowed to react with an enzyme catalyst and a redox mediator comprising the steps of:
(a) applying a potential between the electrodes before or during filling of the cell,
  (b) measuring the increase in current as a function of time,
  (c) determining or predicting from the measurement in step (b) the time of completion of reaction with said catalyst, and
  (d) then interrupting or reversing the polarity of the potential.

BRIEF DESCRIPTION OF THE DRAWINGS

The invention will now be more particularly described by way of example only and with reference to the accompanying drawings wherein:

FIG. 9 describes the cell of FIG. 7 in plan view.

FIG. 10 describes an embodiment of a cell suitable for use in the invention in cross-section view on line 10—10 of FIG. 9.

FIG. 11 describes the cell of FIG. 7 in end section view.

With reference to FIGS. 9, 10 and 11 there is shown (not to scale) by way of example only an electrochemical cell suitable for use in the method of the invention.

Figure 1:
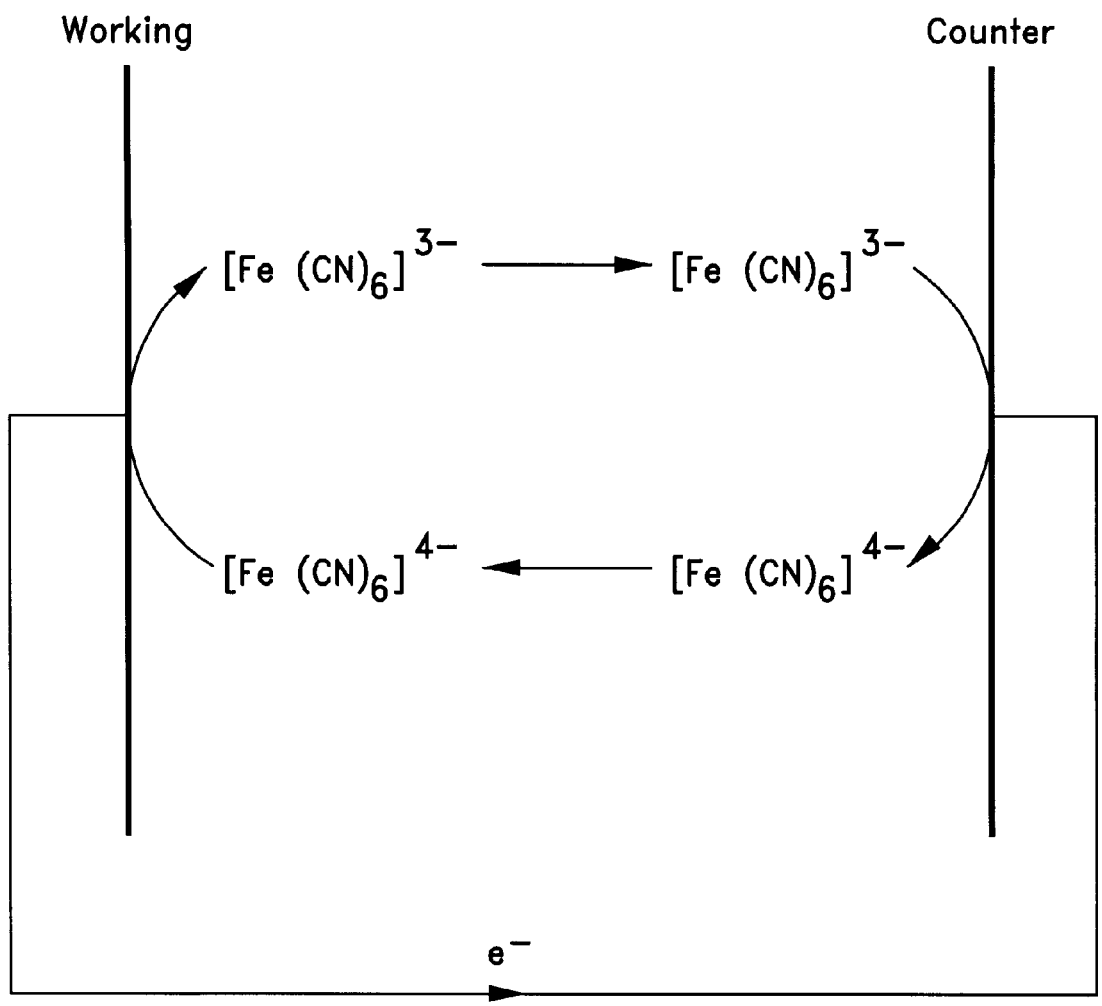
FIG. 1 exemplifies the reactions taking place in a cell according to the invention.

The cell comprises a polyester core 4 approximately 18 mm×5 mm and 100 micron thick and having a circular aperture 8 of 3.4 mm diameter. Aperture 8 defines a cylindrical cell side wall 10. Adhered to one side of core 4 is a polyester sheet 1 having a sputter coating of palladium 2. The sputter coating took place at between 4 and 6 millibar pressure in an atmosphere of argon gas to give a uniform coating thickness of about 100–1000 angstroms. The sheet is adhered by means of an adhesive 3 to core 4 with palladium 2 adjacent core 4 and covering aperture 8.

A second polyester sheet 7 having a second sputter coating of palladium 6 is adhered by means of contact adhesive 5 to the other side of core 4 and covering aperture 8. There is thereby defined a cell having cylindrical side wall 10 and closed each end by palladium metal. The assembly is notched at 9 to provide for a solution to be admitted to the cell or to be drawn in by wicking or capillary action and to allow air to escape. The metal films 2, 6 are connected with suitable electrical connections or formations whereby potentials may be applied and currently measured. The cell is furnished with GOD and ferrocyanide in dry form. The cell is shown schematically in FIG. 1.

In use according to the method a drop of blood is drawn into the cell at 9 by capillary action and allowed to react.

PREFERRED EMBODIMENTS OF THE INVENTION

The electrochemical means for measuring the ferrocyanide concentration after complete reaction can be considered by reference to FIG. 1.

Figure 2:
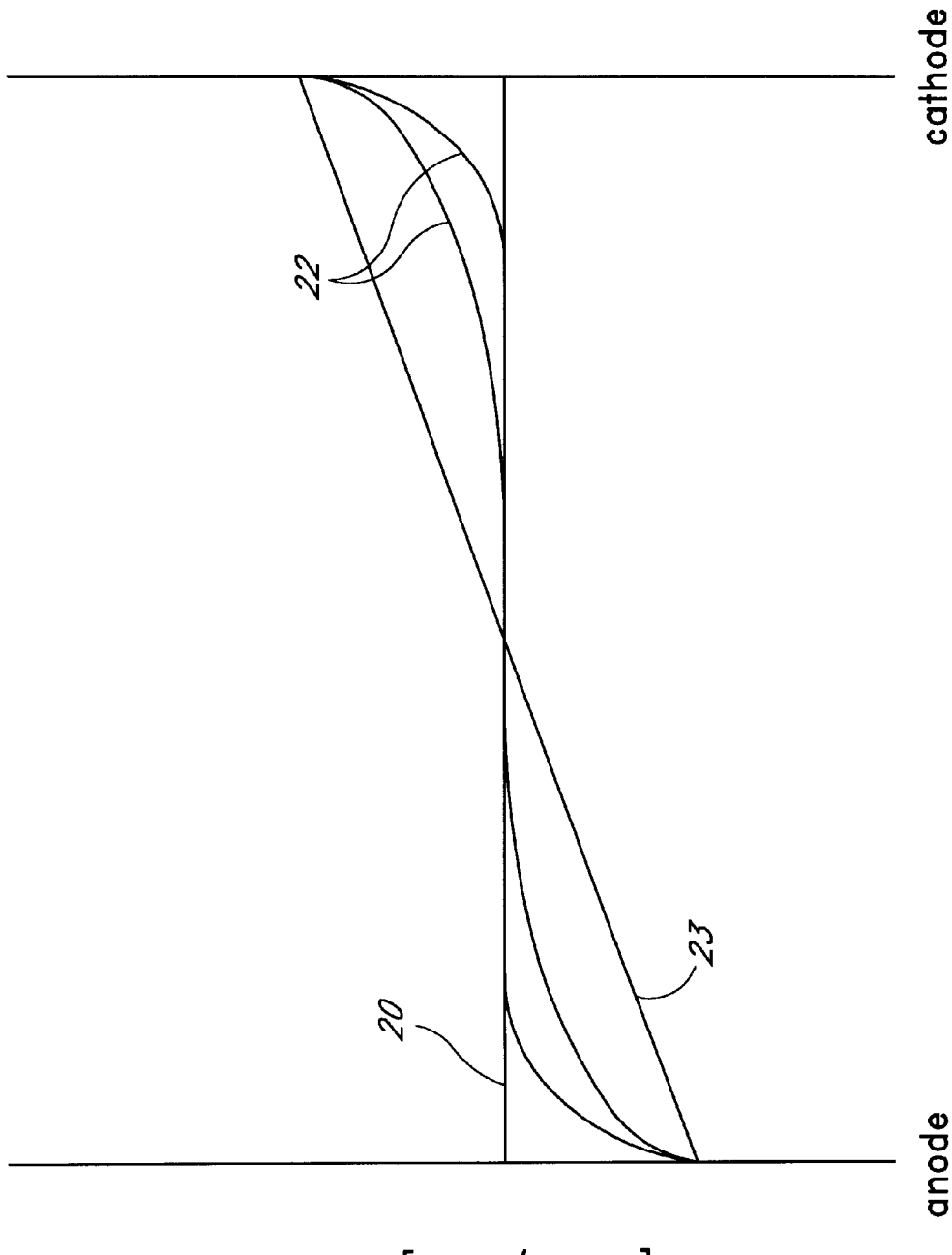
FIG. 2 illustrates the concentration profiles across an electrochemical cell according to the invention before the application of an electrical potential, after application of the potential and prior to reaching steady state, and at steady state.

In a thin layer cell the initial concentration of ferrocyanide and ferricyanide (after 'enzymatic' reaction is complete) is equal throughout the cell (the axis of interest being that between the electrodes). The concentration profile of ferrocyanide is given in FIG. 2.

When a particular potential is applied across the cell ferricyanide is converted to ferrocyanide at the cathode and ferrocyanide is converted to ferricyanide at the anode. The chemistry is so arranged that after complete reaction there is still an excess of ferricyanide compared to ferrocyanide. For this reason the process that limits the complete electrochemical process is the conversion of ferrocyanide to ferricyanide at the anode, simply because ferrocyanide is at a significantly lower concentration. Further the rate limiting step for the reaction of ferrocyanide is the diffusion of ferrocyanide to the anode. After a period of time a steady-state is achieved, wherein the concentration profile of ferrocyanide and ferricyanide remains constant (see FIG. 2).

Therefore there are two limiting situations: initially 20 the ferrocyanide is evenly distributed throughout the cell. Then after a known potential is applied across the cell for a period of time a steady-state concentration profile 23 of ferrocyanide is achieved. The 'transient' 22 reflects the measured current across the cell as the concentration adjusts from the initial situation to the final steady state situation 23. This is shown as a function of time in FIG. 3. It has been found that the change in the current with time during this 'transient' period is dependent upon the total concentration of ferrocyanide and the diffusion coefficient of ferrocyanide.

By solving the diffusion equations for this situation, it can be shown that the transient can be adequately described by the following equation over a restricted calculable time range:

$$\ln\left(\frac{i}{i_{ss}} - 1\right) = -\frac{4\pi^2 Dt}{L^2} + \ln(2) \qquad \text{Eqn 1}$$

where i is the measured current, $i_{SS}$ is the current at steady-state, D the diffusion coefficient of ferrocyanide in the cell, L the separation distance between the anode and cathode, and t is time.

This is a simple solution of the general diffusion equation. However, it may be possible to use other solutions.

The final current at steady state also depends upon the total concentration of ferrocyanide and the diffusion coefficient of ferrocyanide. The steady state current can also be modelled by diffusion theory, and is given by:

$$i_{ss} = \frac{2DFCA}{L} \qquad \text{Eqn 2}$$

where F is the Faraday constant, C the initial concentration of ferrocyanide and A the area of the working electrode. By initial concentration is meant the unperturbed concentration (shown as 20 in FIG. 2).

Analysis of the current observed during the transient and also at steady state allows calculation of both the concentration and diffusion coefficient of ferrocyanide, and thus also the initial glucose concentration.

This analysis is achieved by plotting:

$$\ln\left(\frac{i}{i_{ss}} - 1\right) \qquad \text{Eqn 3}$$

versus time which is substantially linear over a restricted and calculable time range and thus can be analysed for example by linear least squares regression. Since L is a constant for a given cell, measurement of i as a function of time and of $i_{SS}$ thus enables the value of the diffusion coefficient of the redox mediator to be calculated and the concentration of the analyte to be determined.

This is in contrast to the Cottrell current that is measured in the prior art. By measuring the Cottrell current at known times after application of a potential to the sensor electrodes it is only possible to determine the product concentration times square root of the diffusion coefficient. Therefore from the Cottrell current alone it is not possible to determine the concentration of the mediator independent of its diffusion coefficient.

Another possible way to analyse the data is to use the variation of current with time soon after the potential step is applied to the electrodes. In this time period the current can be adequately described by the Cottrell equation. That is:

$$i\text{-FAD}^{1/2}C/(\text{pi}^{1/2}, t^{1/2}) \qquad \text{Eqn 4}$$

By least squares regression on a plot of i vs $1/t^{1/2+1}$ a value of $\text{FAD}^{1/2}C/\text{pi}^{1/2}$ can be estimated from the slope of this plot. The steady state current $i_{SS}$ is given as before, so by combining the slope of the plot given above with the steady state current a value of the concentration of the ferrocyanide, independent of the diffusion coefficient of the ferrocyanide in the cell, can be estimated. This is given by:

$$C=2 \text{ slope}^2\text{pi}/(\text{FALi}_{SS}) \qquad \text{Eqn 5}$$

Figure 3:
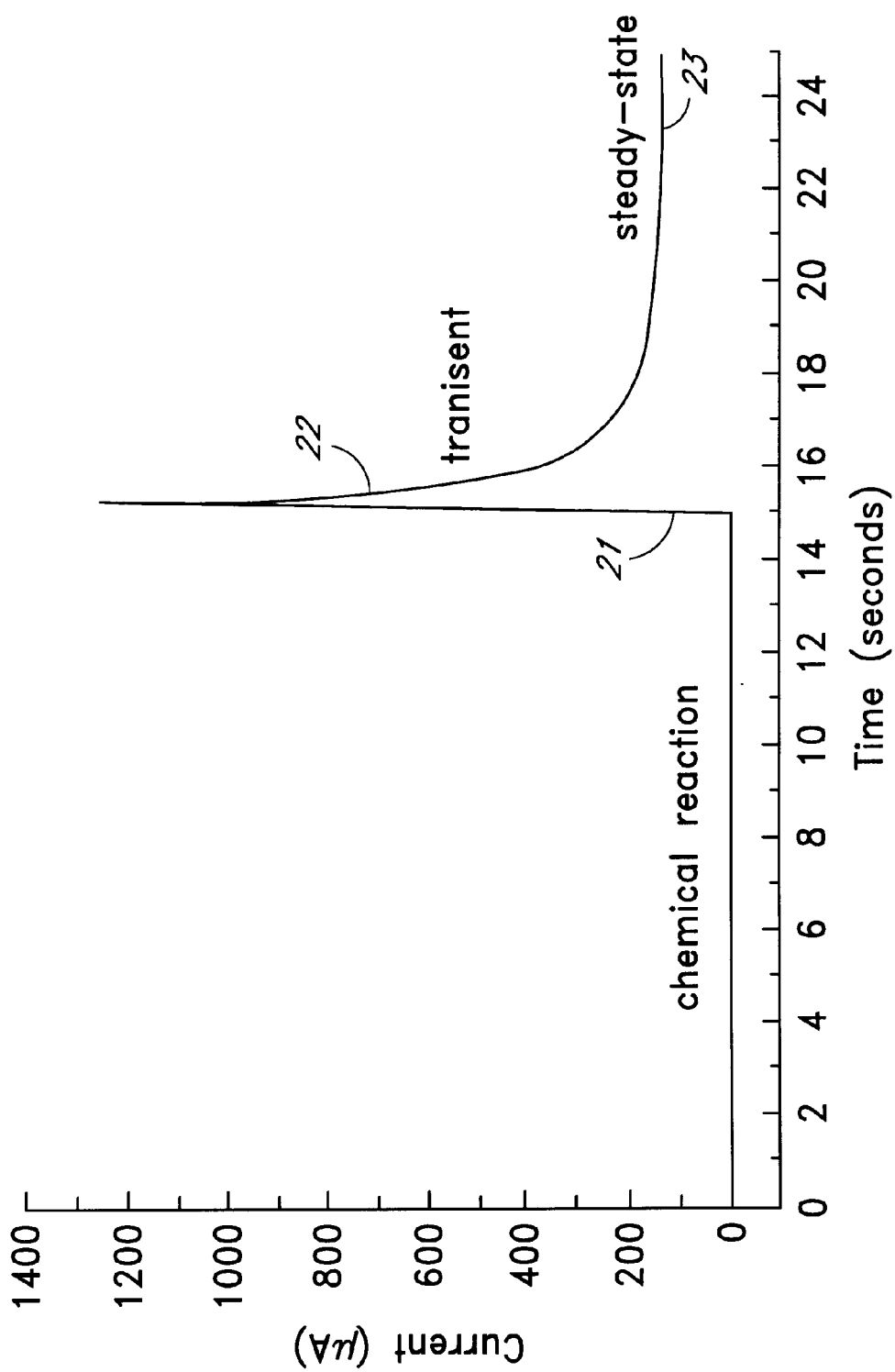
FIG. 3 shows the time dependence of current prior to and after application of electrical potential.
Figure 7:
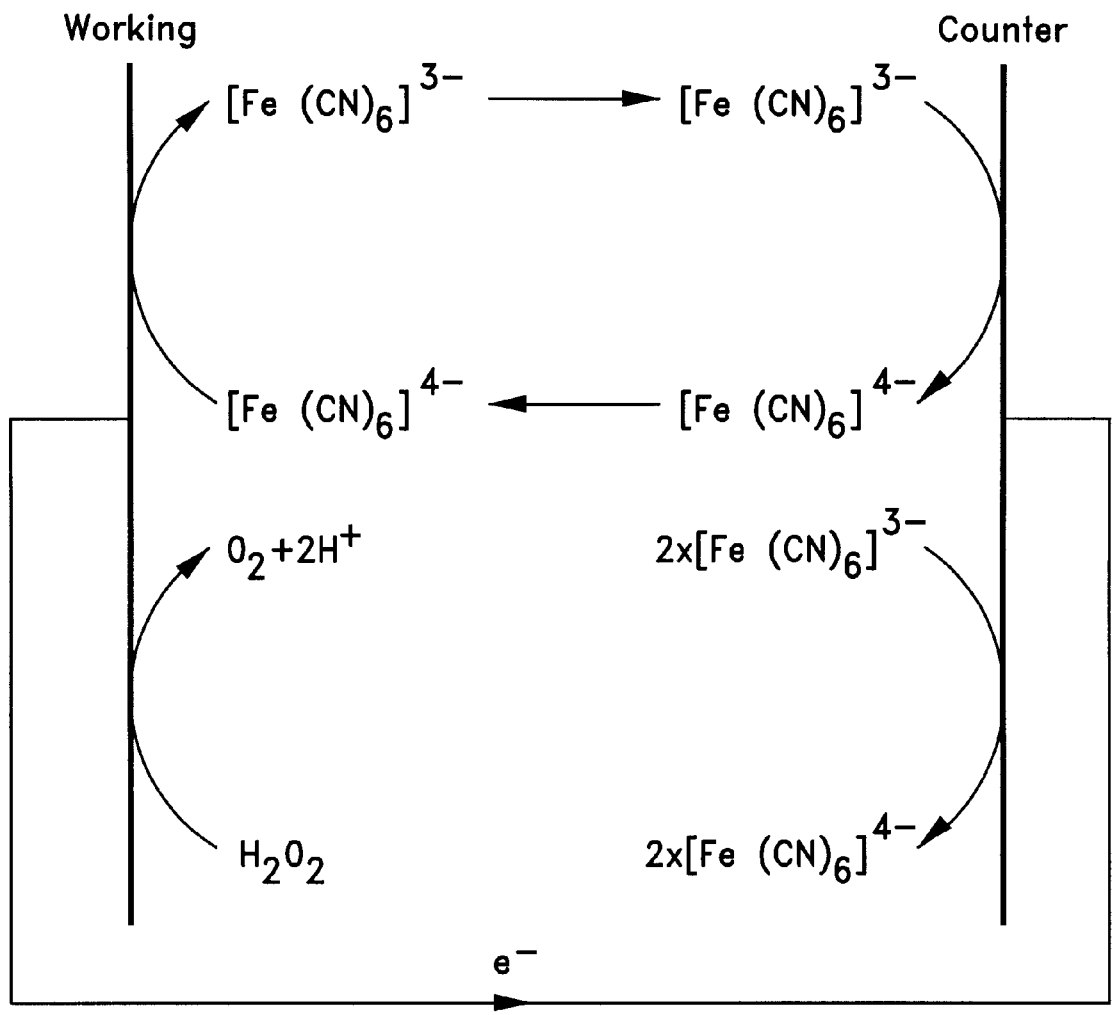
FIG. 7 shows the reactions in an electrochemical cell with peroxide oxidation.
Figure 8:
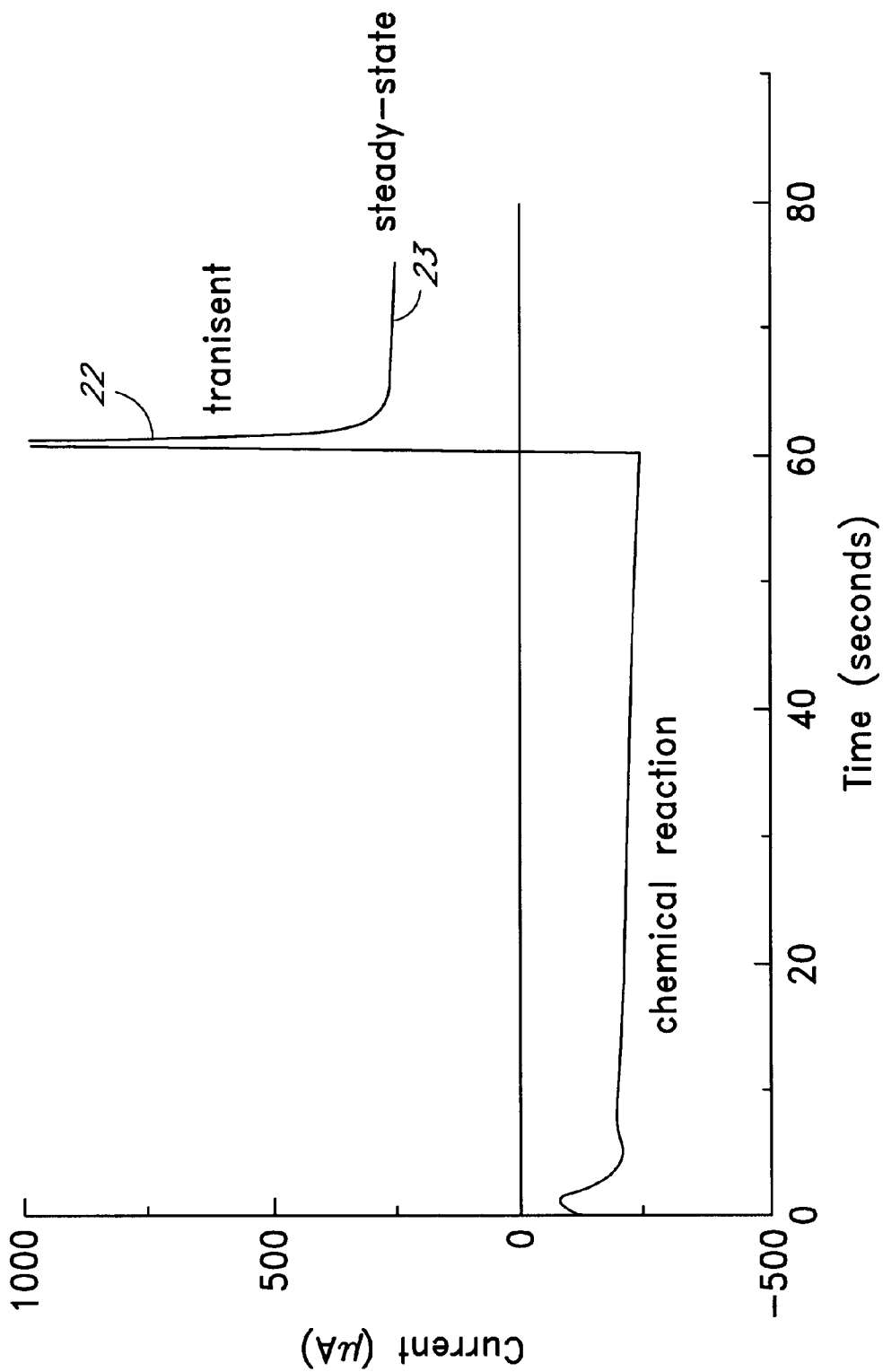
FIG. 8 shows the time dependence of current when an initial potential sufficient to oxidise hydrogen peroxide is applied.

In an example according to the present invention, a sample of blood is admitted to a thin layer cell containing a GOD/ferrocyanide system such as previously described with reference to FIGS. 7, 8 and 9. As illustrated in FIG. 3 after allowing a short time 20 for reaction, an electric potential is applied between the electrodes, current flow commences when the potential is applied 21 but then falls as a transient 22 towards a steady state level 23. The diffusion coefficient and/or glucose concentration are derived by measuring current as a function of time and by estimating the steady state current.

Figure 4:
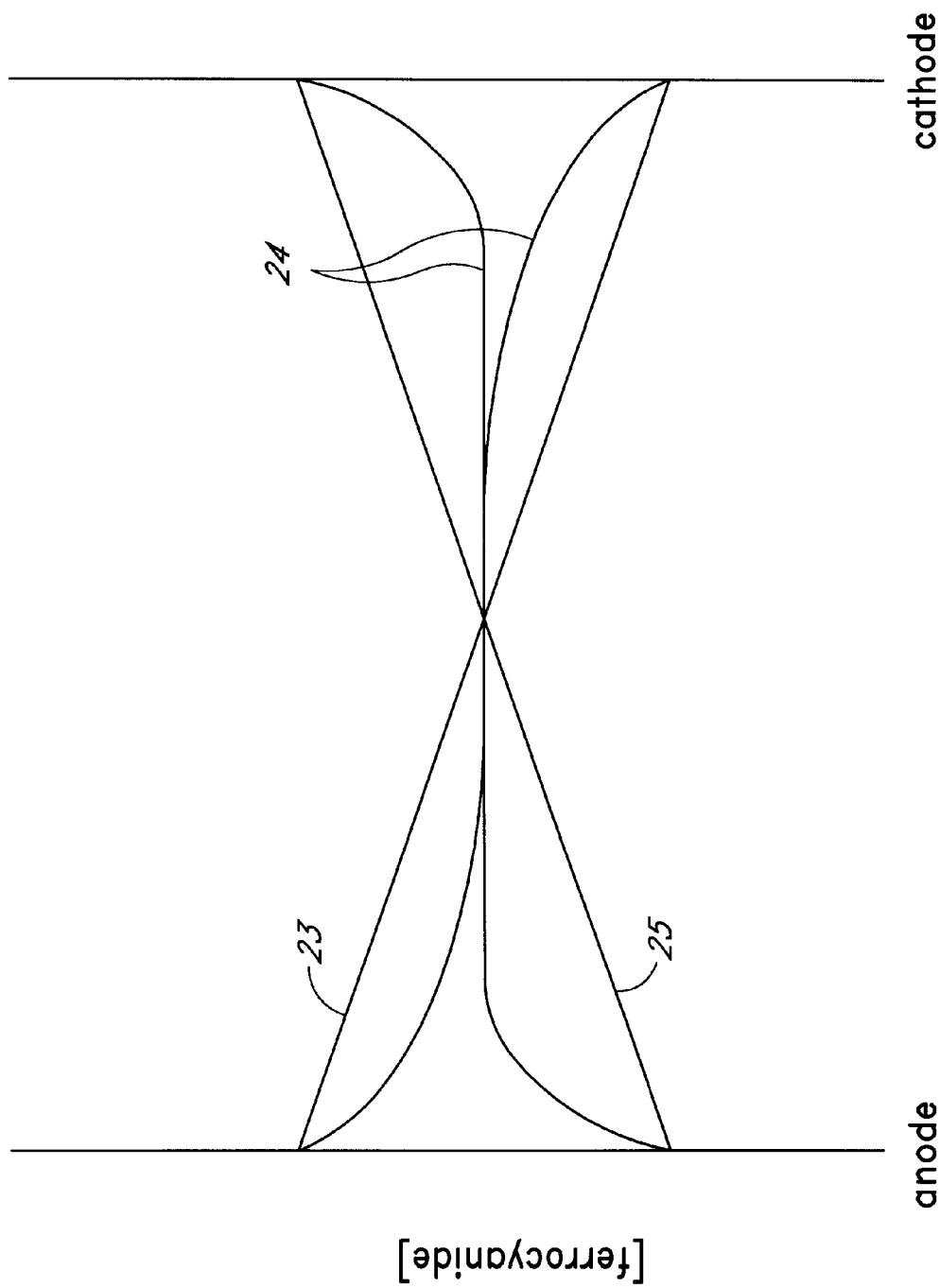
FIG. 4 shows the ferrocyanide concentration profiles across an electrochemical cell according to the invention prior to a polarity reversal, after reversal and prior to reaching a steady state, and at steady state.
Figure 5:
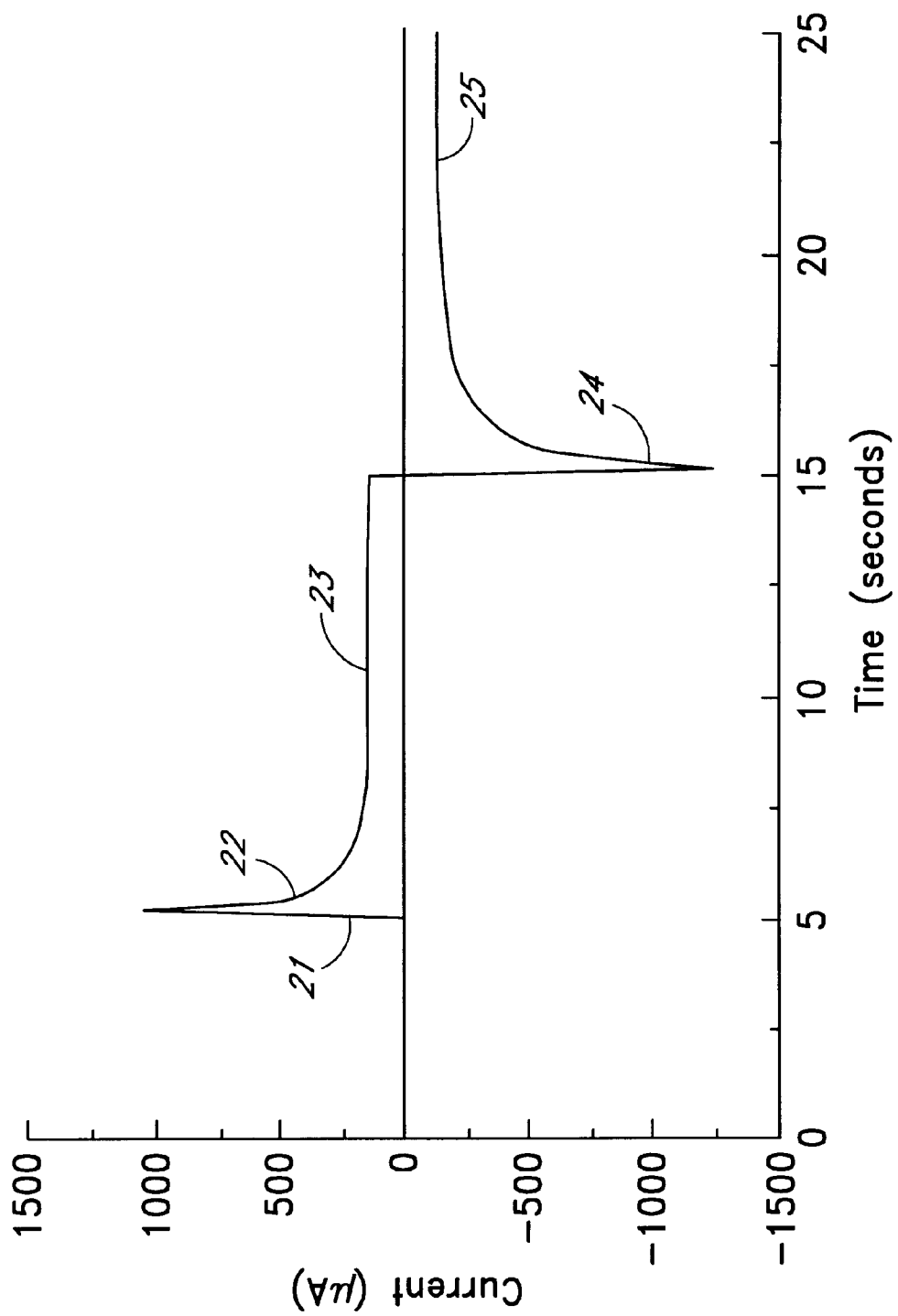
FIG. 5 shows the time dependence of current prior to and after a polarity reversal.

According to the present invention, the current is then interrupted, or reversed in polarity, for example by means of a suitable switch. If the polarity is reversed, a second transient is then observed, and a second steady state is reached after a further period of time although the profile is reversed. The underlying change in ferrocyanide concentration profile across the cell is shown schematically in FIG. 4. The initial concentration profile prior to current reversal is 23. The new steady state concentration profile is shown at 25. The transient concentration profiles are exemplified at 24.

By solving the diffusion equations for this situation, it can be shown that the transient current is described by:

$$\ln\left(\frac{i}{i_{ss}} - 1\right) = -\frac{4\pi^2 Dt}{L^2} + \ln(4) \qquad \text{Eqn 6}$$

It is therefore simple to re-estimate the diffusion coefficient and concentration under the reversed polarity conditions. In theory the results should be independent of the type of transient or polarity. In practice, the results may differ due to factors affecting the transient such as sample inhomogeneity, state of the electrodes, or more importantly, due to asymmetries in the cell construction. This measure is therefore useful for cell diagnosis and also enables greater accuracy by allowing repetitive measurement and averaging with reverse polarities.

Similarly, if the potential is interrupted after steady state is reached, the initial concentration profile will be re-established in a short time (for example 4 seconds).

Figure 6:
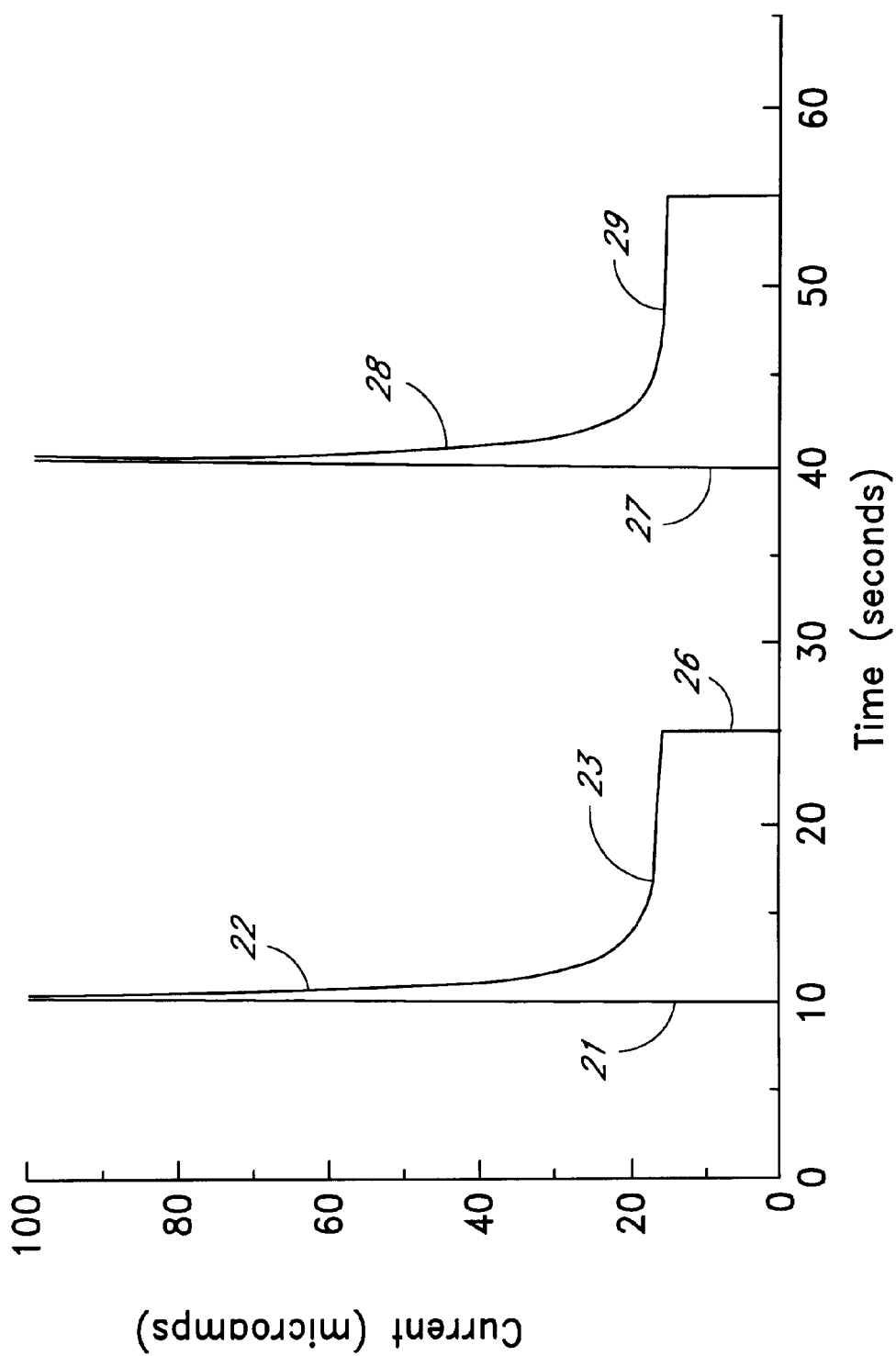
FIG. 6 shows the time dependence of current prior to and after an interruption of applied potential of 15 seconds.

Once the initial state is re-established (or approximated) the potential can be re-applied and the procedure repeated without current reversal. FIG. 6 shows a plot of current versus time similar to that of FIG. 3 but having the potential interrupted at 26 and reapplied after 15 seconds at 27 yielding a new transient current 28 and then a state 29.

As stated previously, the presence of oxygen in the blood is an interference since the concentration of final ferrocyanide is then not directly proportional to the initial glucose. Instead the initial glucose is related both to the final concentration of ferrocyanide plus hydrogen peroxide. However, the present inventors have found that hydrogen peroxide can be oxidised at the anode at a known potential which is higher than that for the ferrocyanide/ferricyanide redox reaction. The total electrochemical path is given in FIG. 7. The hydrogen peroxide reaction is:

hydrogen peroxide → oxygen + 2H$^+$ + 2e$''$      reaction 7

If, during the period of enzyme reaction a potential is applied (FIG. 8) across the cell that is sufficient to oxidise hydrogen peroxide, then the following will happen during that period:

(a) glucose will be reacted to gluconic acid.
(b) ferrocyanide and hydrogen peroxide will result.
(c) the ferrocyanide/ferricyanide redox will eventually reach steady state.
(d) the peroxide will be oxidised at the anode and the electrons used to convert ferricyanide to ferrocyanide.

In total, after a period of time (approximately 2½ seconds in FIG. 8) at a constant potential all the peroxide will be converted to oxygen (which is then a catalyst, and will return to complete more enzyme chemistry until glucose is exhausted), and the electrons utilised to convert ferricyanide to ferrocyanide.

At this stage (60 seconds in FIG. 8) a reverse transient is applied. That is, the polarity of the cells is switched, but now at the lower potential suitable for the ferricyanide/ferrocyanide redox reaction. The final steady state ferrocyanide will once again reflect the initial glucose concentration.

This can be analysed in the previously described manner to determine the total concentration of glucose in the initial sample.

Using the method of the invention the reaction phase of the test can be monitored in situ electrochemically without interfering with the measurement phase. When the reaction is complete one can proceed to measurement without further delay. The wait time will vary from test to test and will be the minimum necessary for any particular sample and cell, taking account of changes in enzyme activity from cell to cell as well as different temperatures and glucose concentrations. This is in stark contrast to prior art in which measurement is delayed until the maximum time required for reaction after allowing for all these factors.

In the present method the reaction phase is monitored by applying a potential between the two electrodes of, for example, $-300$ mV as soon as the cell begins to fill with sample.

For preference the potential is applied continuously from the time that filling of the cell is detected although in less preferred embodiments the potential may be briefly interrupted after the cell begins to fill.

A linear concentration profile of the reduced mediator is soon achieved across the cell. As more reduced mediator is produced by the enzyme reaction with glucose this linear concentration profile becomes steeper and the current increases. When the reaction is complete the current no longer increases. This point can be detected by well known electronic means and the measurement phase of the test can then be commenced.

The end-point of the reaction can also be estimated by fitting a theoretical kinetic equation to the current versus time curve generated during this part of the test. This equation can predict the degree of completion of the reaction at any time, so would allow knowledge of when the end-point would occur without having to wait to get there. This would further shorten the test time. For example, one could fit an equation to the measured prepulse current versus time curve. This equation could then predict that at time X the reaction will be, for example, 90% complete. If one measures the concentration at time X one would then divide the answer by 0.90 to get the true concentration.

The measurement of concentration in this system is done by reversing the potential, ie applying $+300$ mV between the electrodes. A current versus time curve will then occur, which is the same as that of the second transient in a double transient experiment ie by transforming the current i measured during the measurement phase one can obtain a plot of 1 n(i/iss$-$1) versus time which will have a slope of $-4$ pi$^2$ D/1$^2$ and an intercept 1 n(4). The normal analysis can then be used to obtain the concentration of glucose.

As will be obvious to those skilled in the art from the above, instead of fitting a theoretical kinetic equation to the current versus time curve, the end-point of the reaction could also be estimated by fitting an empirical function to at least part of the current versus time curve. This function could allow the extrapolation of the measured current curve to longer times when the reaction is expected to be complete. An example of such an approach is if a curve of the reciprocal of the current is plotted versus the reciprocal of the time and fitted by a straight line. This straight line can then be used to predict the current at longer times when the reaction is expected to be substantially complete. The ratio of the predicted current at longer times to the predicted current appropriate to the concentration measurement phase of the test can then be ascertained. This ratio can be used to correct the estimate of the concentration obtained during the measurement phase to a value concomitant with the reaction substantially reaching end-point.

In some situations it may be difficult or impossible to know the distance between the electrodes in the electrochemical cell. For example, very small separations (ca. 10 microns) may be very difficult to manufacture or measure reproducibly. In these situations the use of information from two adjoining cells can be used to calculate the concentration of an analyte in a sample without knowledge of the cell separation if one of the cells contains a known concentration of the analyte or the corresponding reduced mediator prior to sample addition. Alternatively, a known quantity of this analyte or reduced mediator can be added to the sample destined for one of the two cells prior to addition of the sample to the cell. Another variation is if both cells contain a predetermined analyte or reduced mediator concentration but each has a different concentration. Yet another variation is if two different predetermined quantities of the analyte or reduced mediator are added to two aliquots of the sample, which are then added to the adjoining cells.

As will be apparent to those skilled in the art from the teaching hereof the method is suitable for use with automatic measuring apparatus. Cells of the kind described may be provided with electrical connectors to an apparatus provide with a microprocessor or other programmed electronic control and display circuits which are adapted to make the required measurements perform the required calculations and to display the result. The method may be used to measure the concentration of analytes other than glucose and in liquids other than blood.

The method may be conducted using cells of other design and/or construction and using known catalysts and redox systems other than that exemplified.

For example, other well known prior art reagent systems such as but not limited to those listed in Table 1 may be employed.

TABLE 1

| ANALYTE | ENZYMES | REDOX MEDIATOR (OXIDISED FORM) | ADDITIONAL MEDIATOR |
|---|---|---|---|
| Glucose | GDHpqq | Ferricyanide | |
| Glucose (NAD dependent) | Glucose dehydrogenase and diaphorase | Ferricyanide | |
| Cholesterol | Cholesterol esterase and cholesterol oxidase | Ferricyanide | 2,6-dimethyl-1,4-benzoquinone 2,5-dichloro-1,4-benzoquinone or phenazine ethosulfate |
| HDL cholesterol | Cholesterol esterase and cholesterol oxidase | Ferricyanide | 2,6-dimethyl-1,4-benzoquinone 2,5-dichloro-1,4-benzoquinone or phenazine ethosulfate |
| Triglycerides | Lipoprotein lipase, glycerol kinase, and glycerol-3-phosphate oxidase | Ferricyanide or phenazine ethosulphate | Phenazine methosulfate |
| Lactate | Lactate oxidase | Ferricyanide | 2,6-dichloro-1,4-benzoquinone |
| Lactate | Lactate dehydrogenase and diaphorase | Ferricyanide, phenazine ethosulfate, or phenazine methosulfate | |
| Lactate dehydrogenase | Diaphorase | Ferricyanide, phenazine ethosulfate, or phenazine methosulfate | |
| Pyruvate | Pyruvate oxidase | Ferricyanide | |
| Alcohol | Alcohol oxidase | Phenylenediamine | |
| Bilirubin | Bilirubin oxidase | 1-methoxy-phenazine methosulfate | |
| Uric acid | Uricase | Ferricyanide | |

The two electrochemical cells are then used in the normal fashion, and from each cell the following quantities are measured: steady state current ($i_{ss}$) and the slope of the straight line defined by 1 n($i/i_{ss}-1$) versus time, where i is the measured current. With a knowledge of these values and also a knowledge of the difference in concentration of the analyte or reduced mediator between the two cells, which is known (it is equal to that value purposely added to one cell), it is possible to calculate the concentration of analyte or reduced mediator in the sample, without any knowledge of the separation distance of the electrodes.

The above can be used in conjunction with a third cell that is used to measure the background current or concentration due to current caused by, for example, reduced mediator formed by the application and drying of the chemistry, catalytic effect of the metal surface, oxidation of the metal surface, sample components that have effects on the analyte or mediator, electrochemically responsive components of the sample etc. This background concentration or current would be subtracted from the values measured from the two cells discussed above to calculate the true values for each cell resulting from the analyte in the sample, and in one case also the analyte or reduced mediator purposely added to the cell or the sample.

We claim:

1. A method for determining the concentration of a reduced or oxidized2 form of a redox species in an electrochemical cell of the kind comprising a working electrode and a counter electrode spaced from the working electrode by a predetermined distance, said method comprising the steps of:

(a) applying an electric potential between the electrodes, wherein the electrodes are spaced so that reaction products from the counter electrode arrive at the working electrode by diffusion and wherein the potential of the working electrode is such that the rate of the electro-oxidation of the reduced form or electroreduction of the oxidised form of the redox species is diffusion controlled, (b) determining current as a function of time after application of the potential and prior to achievement of a steady state, (c) estimating the magnitude of the steady state current, (d) interrupting and reapplying, or reversing the polarity, of the potential, (e) repeating step (b) and step (c) to estimate the concentration of the reduced or oxidized form of the redox species.

2. A method according to claim 1 wherein the polarity is reversed in step (d).

3. A method according to claim 1 or claim 2 wherein the electrodes are separated by less than 500 microns.

4. A method according to claim 1 or claim 2 wherein the electrodes are separated by less than 200 microns.

5. A method according to any one of the preceding claims wherein the working electrode extends in a plane parallel to and facing the plane in which the counter electrode extends.

6. A method according to claim 1 or claim 2 wherein a sample is allowed to react with an enzyme catalyst and a redox mediator said method comprising the prior step of operating the cell at a potential higher than that of the redox reaction so as to oxidize hydrogen peroxide at the anode.

7. A method according to claim 1 wherein the potential is reversed repetitively and the concentration of the species is estimated as an average from the result obtained prior to each reversal.

8. A method according to claim 1 wherein the cell contains an enzyme and a redox mediator.

9. A method according to claim 8 wherein the cell contains glucose oxidase.

10. A method according to claim 8 wherein the cell contains ferricyanide.

11. A method according to claim 1 wherein a sample is admitted to the cell and allowed to react to produce an electrochemically oxidizable or reducible species further comprising the steps of:

(a) applying a potential between the electrodes before or during filling of the cell, (b) measuring the change in current as a function of time, (c) determining or predicting from the measurement in step (b) the time of substantial completion of said reaction and/or the magnitude of the measured current upon substantial completion of said reaction, (d) then interrupting and reapplying, or reversing the polarity of, the potential, (e) then determining current as a function of time after reapplication or reversal of the potential and prior to achievement of a steady state, (f) estimating the magnitude of the steady state current, and (g) from the results of steps (c), (e) and (f) estimating the concentration of an analyte in the sample.

12. A method according to claim 11 further comprising a second cell containing a known concentration of analyte or reduced mediator and wherein the second cell is used to calibrate the first.

13. A method according to claim 11 wherein a known concentration of analyte or reduced mediator is added to the analyte and used for calibration.

14. A method according to claim 11 wherein the potential is applied between the electrodes continuously between step (a) and step (c).

* * * * *